US006964603B2

(12) United States Patent
Fischer et al.

(10) Patent No.: US 6,964,603 B2
(45) Date of Patent: *Nov. 15, 2005

(54) FIBER FLOCKED DENTAL POLISHING TIPS

(75) Inventors: Dan E. Fischer, Sandy, UT (US); Paul Lewis, Midvale, UT (US)

(73) Assignee: Ultradent Products, Inc., South Jordan, UT (US)

( * ) Notice: Subject to any disclaimer, the term of this patent is extended or adjusted under 35 U.S.C. 154(b) by 47 days.

This patent is subject to a terminal disclaimer.

(21) Appl. No.: 10/103,528

(22) Filed: Mar. 21, 2002

(65) Prior Publication Data

US 2003/0181154 A1 Sep. 25, 2003

(51) Int. Cl.⁷ .............................................. B24D 11/00
(52) U.S. Cl. ...................... 451/532; 451/529; 433/125; 433/166; 15/167.1; 15/207.2
(58) Field of Search ................................. 451/532, 537, 451/526, 490, 527, 529; 433/114–116, 125, 433/166; 15/167.1, 207.2

(56) References Cited

U.S. PATENT DOCUMENTS

| | | | | |
|---|---|---|---|---|
| 1,907,286 A | * | 5/1933 | Chott | ........................... 15/110 |
| 2,451,918 A | | 10/1948 | Chott | |
| 2,842,844 A | * | 7/1958 | Seal | ............................ 451/529 |
| 4,527,575 A | | 7/1985 | Vasas | |
| 4,561,214 A | * | 12/1985 | Inoue | ............................. 451/1 |
| 4,869,277 A | | 9/1989 | Olsen | |
| 4,958,402 A | * | 9/1990 | Weihrauch | ................. 15/207.2 |
| 5,360,339 A | | 11/1994 | Rosenberg | |
| 5,369,916 A | * | 12/1994 | Jefferies et al. | .............. 451/532 |
| 5,380,202 A | | 1/1995 | Brahler | |
| 5,405,265 A | | 4/1995 | Mendoza | |
| 5,584,690 A | | 12/1996 | Maassarani | |
| 5,652,990 A | * | 8/1997 | Driesen et al. | ................. 15/28 |
| 5,775,905 A | | 7/1998 | Weissenfluh et al. | |
| 5,797,744 A | | 8/1998 | Rosenberg | |
| 5,827,064 A | * | 10/1998 | Bock | .......................... 15/167.1 |
| 5,882,201 A | * | 3/1999 | Salem | .......................... 433/216 |
| 5,944,519 A | * | 8/1999 | Griffiths | ....................... 433/80 |
| 6,049,934 A | | 4/2000 | Discko | |
| 6,059,570 A | * | 5/2000 | Dragan et al. | ................. 433/80 |
| 6,099,309 A | * | 8/2000 | Cardarelli | .................... 433/125 |
| 6,146,140 A | | 11/2000 | Bailey | |
| 6,286,246 B1 | * | 9/2001 | Rachal et al. | ............... 43/42.25 |
| 6,312,257 B1 | * | 11/2001 | Aschmann et al. | ......... 15/167.1 |
| 6,343,929 B1 | * | 2/2002 | Fischer | ........................ 433/81 |
| 6,446,294 B1 | * | 9/2002 | Specht | ........................ 15/22.1 |
| 6,554,614 B1 | * | 4/2003 | Dubbe et al. | ............... 433/125 |
| 6,638,067 B2 | * | 10/2003 | Fischer et al. | .............. 433/102 |

* cited by examiner

*Primary Examiner*—Hadi Shakeri
(74) *Attorney, Agent, or Firm*—Workman Nydegger

(57) ABSTRACT

A dental polishing tip is adapted to be coupled to a dental drive apparatus. The apparatus rotates the tip, thereby polishing the teeth. The tip includes: (i) a post having a proximal end and an opposing distal end, the proximal end being adapted to be coupled to the dental drive apparatus; (ii) an electrostatically flocked polishing head. The electrostatic flocking material on the polishing head at least temporarily increases the retention of the polishing material on the polishing head, thereby deceasing splattering.

8 Claims, 7 Drawing Sheets

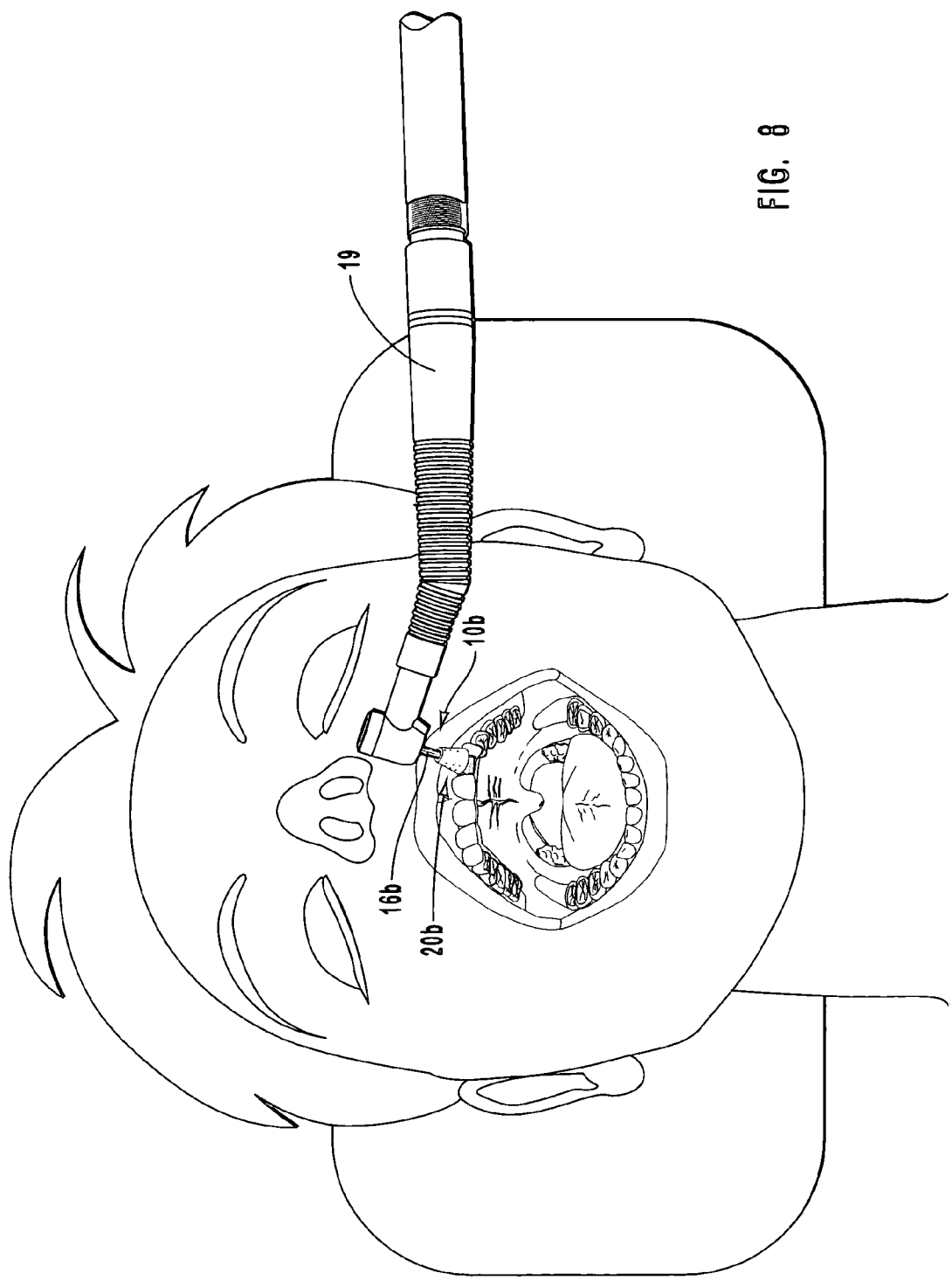

FIBER FLOCKED DENTAL POLISHING TIPS

THE FIELD OF THE INVENTION

This invention is in the field of dental polishing tips that are employed to apply polishing materials to the teeth of a patient as part of a dental polishing procedure.

BACKGROUND

Polishing tips such as those commonly referred to as dental polishing cups are typically used in dental polishing procedures. Such polishing tips typically comprise a rigid, elongate metal post coupled to a flexible polishing head having the shape of a cup which can be loaded with prophylaxis polishing material. Such a post typically has: (i) one end that is adapted to couple to a handpiece that is held by a dentist during a dental procedure, and (ii) another end that is coupled to the flexible cup. The handpiece has a rotating member that rotates the polishing tip as the dentist presses the loaded flexible cup against the teeth of a patient during a dental procedure. The cup is thereby rotated at high speed during the cleaning and polishing of the teeth.

Since the loaded polishing cup is rotated at high speed, the cup is prone to splatter prophylaxis material as it is applied to the teeth of a patient. This splattering is an inefficient use of the material and can leave deposits of material within the patient's mouth, on the patient's face and clothing or within the dental office. Consequently, what is therefore needed is a polishing tip configured to more efficiently apply prophylaxis material to the teeth of a patient.

Another challenge in the art is that sometimes polishing heads can create too much friction against a tooth surface. This can result from the surface contact of a high friction polishing head (e.g., a rubber polishing head) against a tooth. Such friction can cause excessive heat on a tooth, which can injure a tooth or cause pain and can prevent a high polish or mar the surface of the tooth. Consequently, what is also needed is a method for applying paste to a tooth surface, without overly polishing the tooth.

OBJECTS AND SUMMARY OF INVENTION

A polishing tip of the present invention is configured for use during a dental polishing procedure. The tip can be coupled to a dental drive apparatus such that the apparatus can be used to polish the teeth of a patient.

One such polishing tip includes: (i) a post having a proximal end and an opposing distal end, the proximal end being adapted to be coupled to the moving (e.g., rotating) portion of a dental drive apparatus; and (ii) a flocked polishing head. The flocked polishing head comprises: (A) a polishing head substrate coupled to the distal end of the post, (B) an adhesive layer formed on at least a portion of the polishing head substrate; and (C) flocked fibers coupled by the adhesive onto the polishing head substrate. The flocking of the head substrate preferably occurs through an electrostatic flocking process.

The polishing head is capable of receiving a prophylaxis polishing paste thereon and is configured to be placed adjacent the teeth of a patient in order to apply the paste to the teeth of the patient and polish the patient's teeth.

The flocked fibers at least temporarily increase the retention of the prophylaxis material on the polishing head, thereby decreasing splattering. The prophylaxis material can temporarily cling to the fibers, thereby increasing retention of the material on the head. The individual fibers mounted on the head substrate also combine to form a collective support structure that can increase retention of the prophylaxis material on the head by entrapping paste between adjacent fibers. By protruding outwardly away from their adhesion site on the substrate, the collective fibers form a convenient network of fibers that can at least temporarily maintain prophylaxis material therein.

The fibers also prevent the polishing of the teeth with too much friction by (i) preventing too much contact between the high friction polishing head and the tooth and (ii) by ensuring that more paste material is between the teeth and the polishing head. Furthermore, in one embodiment, the flocking fibers (comprising, e.g., nylon or polyester) tend to have less friction than the materials employed for the polishing head substrate, (comprising, e.g., an elastomeric material, such as a thermoplastic synthetic rubber material). Also in one embodiment, the head substrate is covered with an adhesive to which the flocked fibers are attached such that the tooth is contacted by the paste material, flocked fibers, and/or the adhesive, thereby insulating the tooth from the polishing head substrate itself.

While the polishing head substrate may have an abrasive material impregnated therein, in one embodiment, the polishing head substrate comprises an elastomeric material without an abrasive impregnated therein.

Thus, one aspect of the invention is to provide an improved polishing tip. Another aspect of the invention to provide a polishing tip that is more efficient. Another aspect of the invention to provide a polishing tip that does not splatter a significant amount of prophylaxis paste during a dental procedure. Another aspect of the invention to provide a polishing tip that prevents the application of paste on a tooth with too much friction against the surface of a tooth.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 8 is a view of a dental drive apparatus being employed in a polishing procedure using a tip of the present invention, such as shown in FIG. 1.

FIG. 1 demonstrates a plurality of electrostatically flocked polishing tips of the present invention that can be employed in a dental polishing procedure. The first tip 10 is an example of an electrostatically flocked polishing cup tip. The second tip 12 is an example of an electrostatically flocked polishing disk tip. The third tip 14 is an example of an electrostatically flocked polishing tip comprising a point. As discussed below, by employing flocked tips, a variety of advantages are achieved, such as at least temporarily increasing retention of polishing paste on a tip during a polishing procedure, and thereby decreasing splattering.

One of the advantages of electrostatic flocking in this context is that by electrostatically flocking each head substrate, the fibers are applied in a uniform manner substantially perpendicular to their adhesion site on the head substrate. Consequently, adjacent fibers are substantially parallel to each other. Such substantially parallel fibers can be densely and uniformly applied and can at least temporarily retain paste between the fibers.

Electrostatically flocked polishing tip 10 comprises a rigid, elongate post 16 (comprising, e.g., a metallic or plastic material, such as polycarbonate, for example) having a proximal end 18 adapted to be coupled (e.g., removably coupled) to a moving (e.g., rotating) member of a dentist's drive apparatus. An example of such a drive apparatus having a moving (e.g., rotating) member is a handpiece 19, such as shown in FIG. 8.

Figure 1:
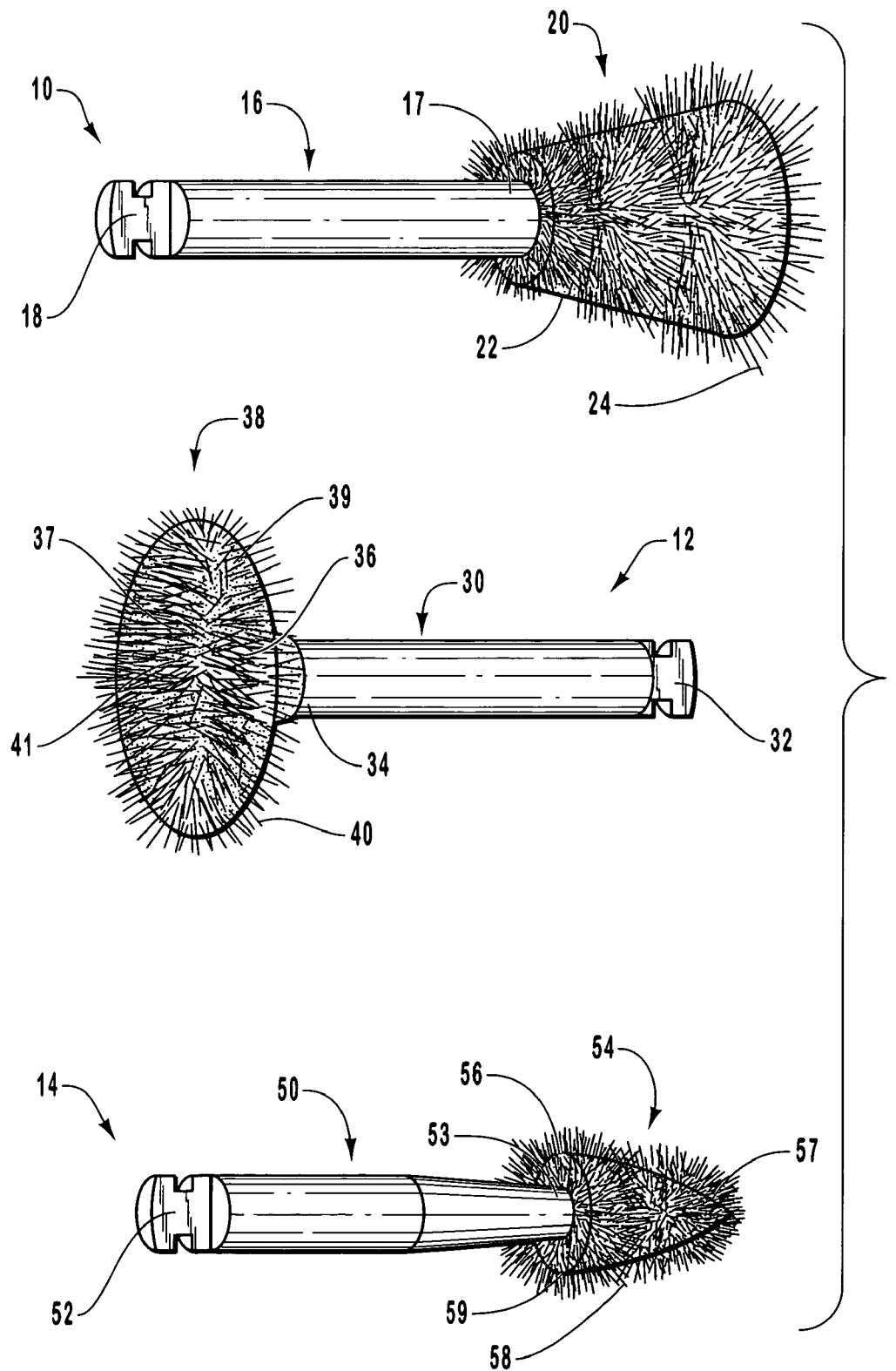
FIG. 1 is a view of a plurality of electrostatically flocked dental polishing tips of the present invention.

For example, proximal end 18 may be adapted to be so coupled to the drive apparatus by having notches, one or more grooves, and/or cutaway portions therein, such as shown in FIG. 1, that correspond to a receiving portion of the rotating member. A vast array of other configurations are also available that enable proximal end 18 to be coupled to a handpiece or other dental drive apparatus.

Coupled to the distal end 17 of post 16 is a polishing head 20. The portion of distal end 17 of post 16 that is coupled within polishing head 20 may have a variety of different configurations that facilitate the coupling of the head 20 thereto, such as by being split or by being enlarged and/or flattened and having one or more grooves therein.

Figure 2:
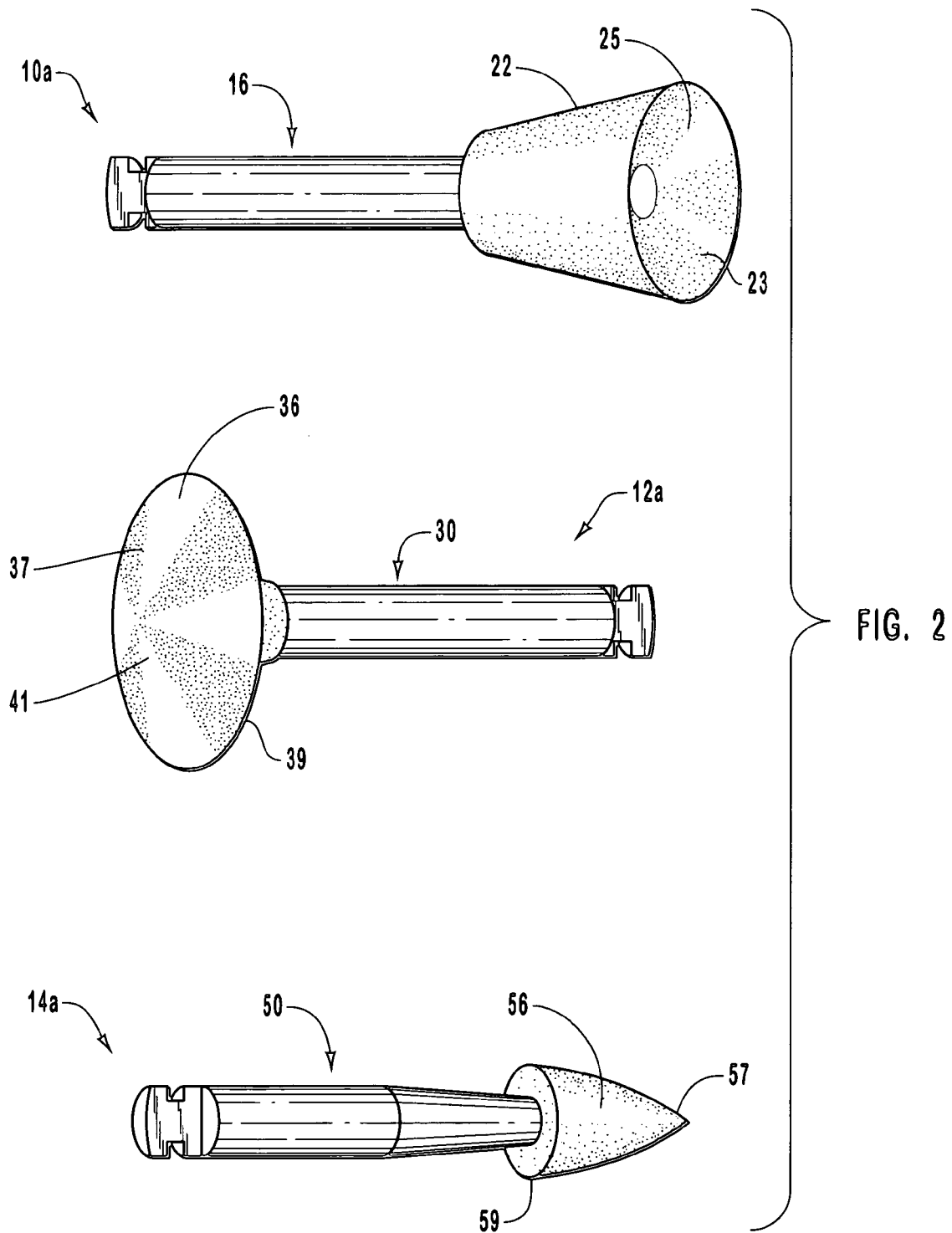
FIG. 2 is a view of the tips of FIG. 1 prior to the placement of the flocking material thereon.

As further shown in FIGS. 1 and 2, head 20 comprises an underlying head substrate 22 which has an electrostatic flocking material 24 coupled thereto. Head 20 has the configuration of a cup that has a concave portion 25 in the head substrate 22 thereof, as shown in FIG. 2. Head 20 receives polishing paste from a reservoir and is pressed against the teeth to thereby polish the teeth.

Substrate 22 may comprise a variety of different materials, such as a flexible material, e.g., a plastic, natural rubber, silicon rubber, SANTOPRENE, thermoplastic synthetic rubber having a durometer of about 40 to about 75, or other elastomeric material, such a moldable elastomeric material, e.g., an injection moldable, insertion moldable, or compression moldable elastomeric material, or another elastomeric material. While the polishing head substrate may have an abrasive material impregnated therein, in one embodiment, the polishing head substrate comprises an elastomeric material without an abrasive impregnated therein. Thus, a polishing cup having no abrasive material therein is one example of a polishing tip of the present invention.

A variety of other shapes which are suitable for coupling to a post and polishing the teeth of a patient may also be employed in the present invention. As shown in FIG. 1, the head substrate can have a variety of different shapes including cup shapes, disk shapes, pointed shapes, round shapes, square shapes, triangle shapes, star shapes, elliptical shapes, ball shapes, spherical shapes and a variety of other shapes that may assist the head substrate in performing a polishing procedure.

The flocked fibers 24 coupled to head substrate 22 at least temporarily increase the retention of the polishing material on polishing head 20 during a polishing procedure, thereby deceasing splattering. The polishing material can temporarily cling to the fibers, thereby increasing retention of the material on the head 20. The individual fibers 24 combine to form a collective support structure that can increase retention of the prophylaxis material on the head by entrapping paste between adjacent fibers. The fibers 24 also prevent the polishing of the teeth with too much friction by preventing too much contact between the polishing head substrate and the tooth and by ensuring that more paste material is between the teeth and the polishing head.

Tips 10, 12 and 14 may have heads comprising the same or similar materials, for example, although the heads of the tips have different shapes. Thus, electrostatically flocked polishing tip 12 comprises a rigid post 30 having a proximal end 32 adapted to be coupled to a rotating member of a dentist's drive apparatus. Coupled to the distal end 34 of post 30 is a polishing head 38, which is in the form of a disk. Head 38 comprises an underlying substrate 36, such as a flexible material as discussed above, and an electrostatic flocking material 40 coupled thereto.

Furthermore, electrostatically flocked polishing tip 14 comprises a rigid post 50 having a proximal end 52 which is adapted to be coupled to a rotating portion of a dental drive apparatus. Coupled to the distal end 53 of post 50 is a polishing head 54, which, in the embodiment of FIG. 1, is in the form of a point. Head 54 comprises an underlying substrate 56, such as a flexible material, and an electrostatic flocking material 58 coupled thereto. Tips 10, 12 and 14, as well as tips having a variety of other head shapes, can also receive polishing material thereon and be pressed at high speeds against the teeth of a patient during a polishing procedure.

With respect to tip 12, fibers 40 are present throughout at least the front side 37 of head substrate 36, and optionally on both front and back sides. However, in another embodiment (not shown), the fibers are located in the central portion 41 of the head substrate 36, but are not located at the outer rim 39 thereof and do not extend past outer rim 39, in an effort to prevent the fibers from whipping the gums of a patient. Similarly, in another embodiment (not shown), fibers 58 are located on the distal tip portion 57 of head substrate 56, but not at or near the rim 59 thereof to help prevent the fibers from whipping the gums of a patient.

FIG. 2 demonstrates examples of non-flocked tips 10a–14a that may be flocked to form respective electrostatically flocked tips 10–14. Flocking may advantageously be performed through an electrostatic process, such as discussed below. As shown, each nonflocked tip 10a–14a comprises a post 16, 30, 50 having a respective nonflocked head substrate 22, 36, 56 coupled thereto. Substrate 22 has a cavity 25 therein such that a cup shape is formed, such as a prophylaxis polishing cup. Fibers are flocked onto the interior surface 23 of cavity 25. In one embodiment, a tip in the form of a cup is flocked only in the cavity 25 thereof, as will be discussed below.

The flocked tips of the present invention are preferably formed at least partially through the use of electrostatic flocking. However, in another embodiment, the tips may be flocked through other flocking methods such as gravity sprinkling or in another manner, depending upon the desired performance required. For example, it may be possible to adhere certain fibers by hand or by blowing them onto a head substrate with air onto an adhesive for example.

Electrostatic flocking is preferred, at least in part, because it is a convenient, efficient flocking method and because fibers can be evenly placed onto the head substrate. Also, the fibers can be placed thereon in an orientation that is substantially perpendicular to the substrate surface, achieving a variety of different advantages. For example, the fibers can be applied in a manner such that adjacent fibers are substantially parallel to each other with the free ends extending away from the surface of the head substrate. Paste can be retained in the spaces between parallel fibers. Furthermore, with electrostatic flocking, fibers can be densely applied if desired or less densely if desired. The fibers also provide an additional abrasive effect as the tip head is rotated at high speed against the teeth.

Figure 3:
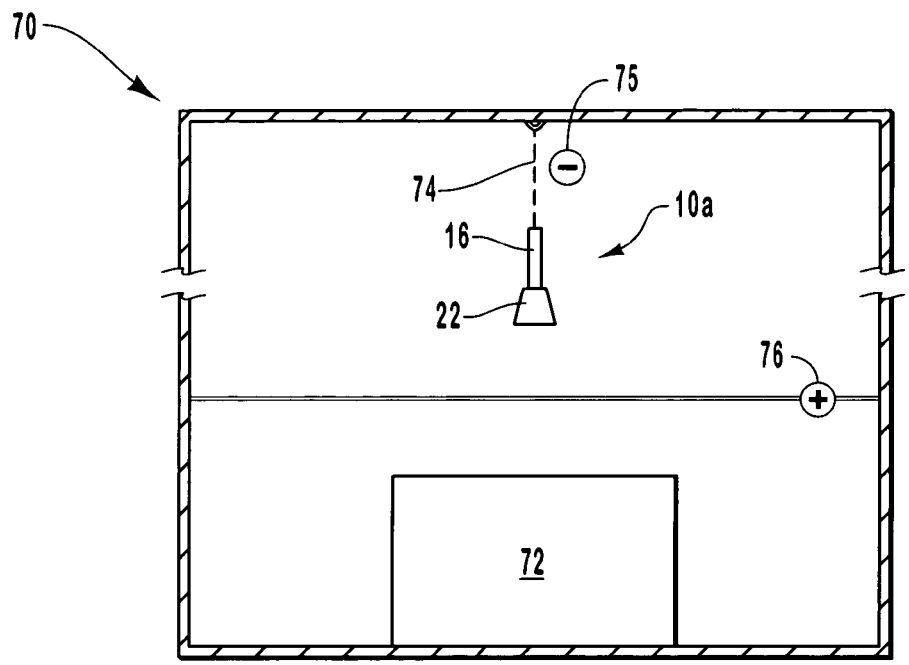
FIG. 3 is a schematic view of an unflocked tip of FIG. 2 placed in an electrostatic flocking chamber in preparation for electrostatically flocking the tip.

FIGS. 3–6 depict a schematic representation of one of a variety of different possible methods for electrostatically flocking a dental polishing tip 10a–14a. FIG. 3 shows a schematic depication of a flocking chamber 70. Flocking chamber 70 has a source 72 of flocking fibers and a polishing tip holder 74. Flocking chamber 70 further has a negative electrode 75, which can be integrally coupled to a tip holder 74 or coupled thereto in another manner, for example, and a positive electrode represented at 76. In one embodiment, negatively charged tip holder 74 selectively holds an unflocked tip 10a within flocking chamber 70.

Figure 4:
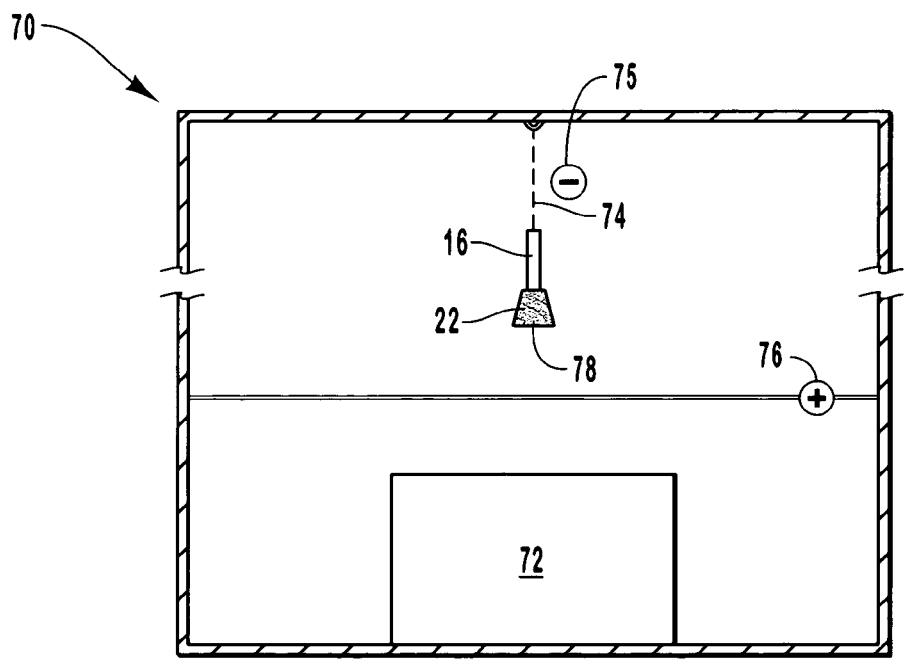
FIG. 4 features a schematic representation of an adhesive placed onto the polishing head substrate of FIG. 3.

As represented in FIG. 4, in order to cause fibers to adhere to each polishing head substrate 22, an adhesive layer 78 is first formed on the head substrate 22, such as by placing an adhesive 78 on the head substrate 22. Optionally, a solvent may be placed onto the polishing head substrate 22, thereby forming an adhesive layer if certain substrate material is employed. FIG. 74 depicts head 22 having an adhesive layer 78 on the outer surface thereof.

The adhesive layer 78 is formed on at least a portion of outer surface of head substrate 22, depending on the amount of fiber coating which is desired. That portion of head substrate 22 which has an adhesive layer thereon will receive fibers thereon such that the fibers adhere thereto even when the electrostatic charge is ceased. However, portions of head substrate 22 lacking an adhesive layer will not have fibers adhered thereto when the electrostatic charge ceases.

Figure 5:
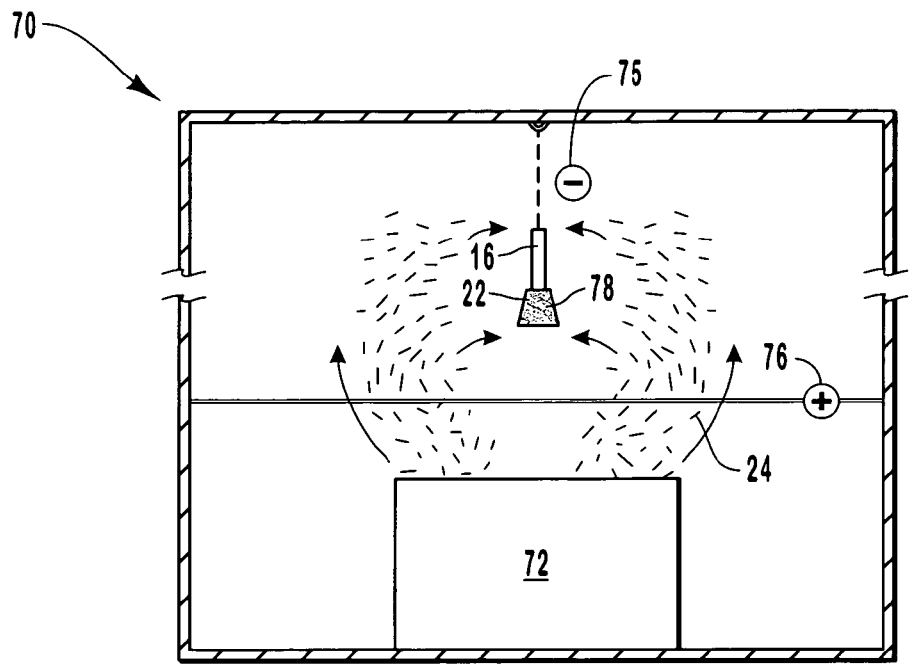
FIG. 5 is a schematic representation of a flocking material being released from a flocking material source in order to electrostatically flock an adhesive laden dental polishing head substrate of the present invention.

With reference now to FIG. 5, a schematic depiction of the electrostatic deposition of fibers 20 onto adhesive layer 78 is shown. One skilled in the art will appreciate that FIG. 4 depicts a technique known as "up flocking". However, a variety of different methods for electrostatically depositing a plurality of fibers to the outer surface 29 of head substrate 22 may be employed in the present invention. Such alternative methods include down flocking, side flocking, flocking at an angle, or a variety of different electrostatic flocking methods.

As an electrostatic charge is actuated within flocking chamber 70, fibers 24 are delivered to head substrate 22 from fiber source 24. The adhesive 78 is then allowed to harden, adhering fibers 24 to head substrate 22. By depositing fibers 24 in an electrostatically charged environment, fibers 24 can be applied in a uniform manner.

Figure 6:
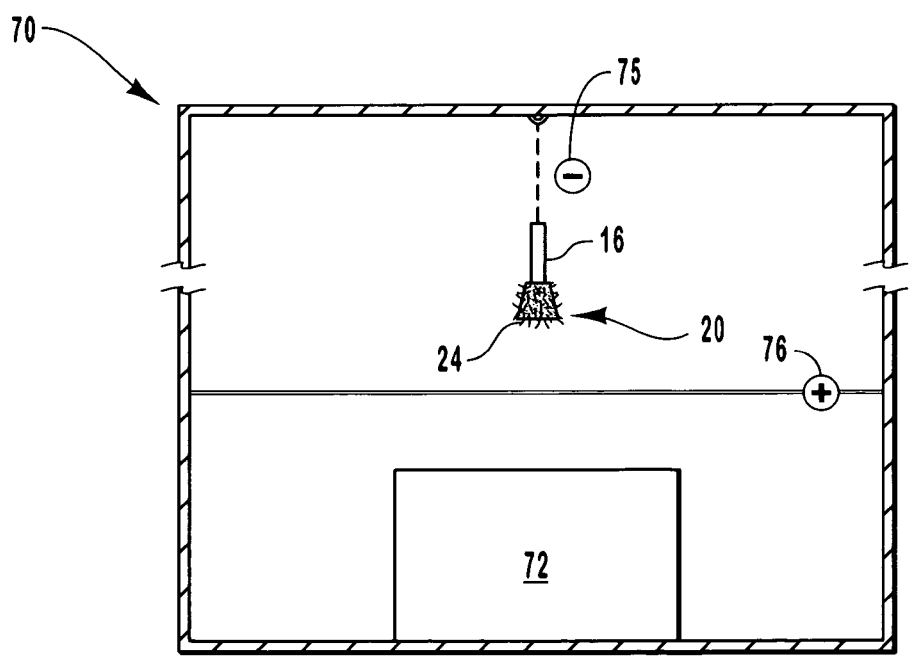
FIG. 6 is a schematic representation of an electrostatically flocked tip of the present invention.

FIG. 6 depicts head substrate 22 having electrostatically deposited fibers 24 on the outer surface thereof to form polishing head 20. Fibers 24 are coupled at their adhesive ends by adhesive layer 78 to head substrate 22. The opposing free ends of flocking fibers 20 extend away from the head substrate 22.

Thus, as depicted in FIGS. 1, 5, 6 (and 7A–7C), each electrostatically flocked polishing tip head (e.g., 20, 38, 54, 20b) comprises (i) a head substrate 22; (ii) an adhesive layer 78 formed on the head substrate; and (iii) a plurality of flocking fibers 24 electrostatically deposited onto the adhesive layer 78.

Figure 7A:
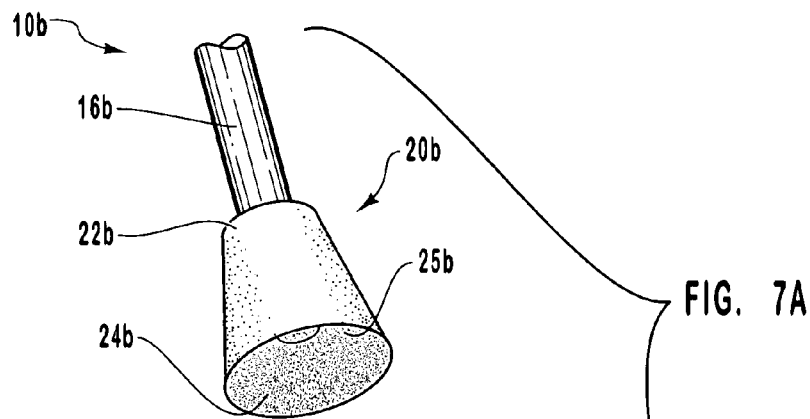
FIG. 7A is a cutaway view of an alternative electrostatically flocked dental polishing tip being placed within a polishing paste reservoir 80 to thereby load the tip with polishing paste 82.
Figure 7B:
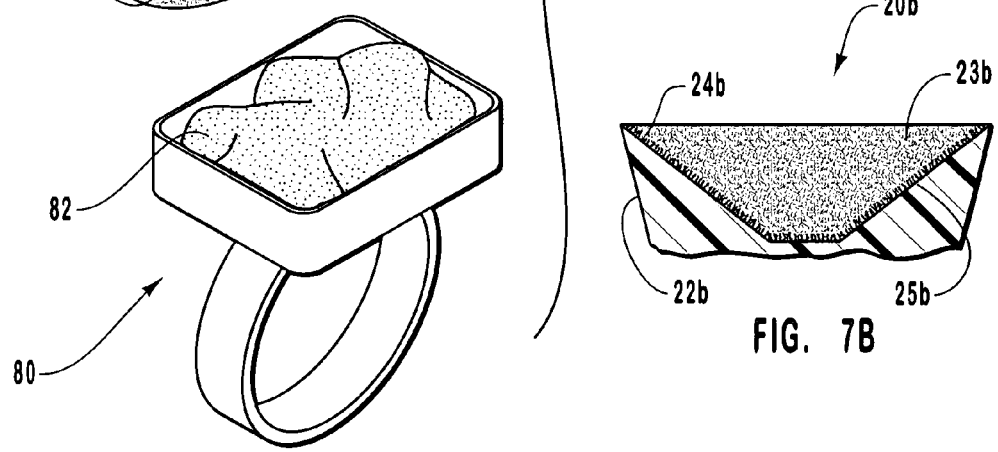
FIG. 7B is a cutaway view of the tip of FIG. 7A illustrating the flocked surface of the head substrate.

As shown in FIGS. 7A and 7B, in one embodiment, the flocking fibers 24b are located only within the inner cavity 25b of the polishing head substrate 22b, thereby preventing the fibers 24b of polishing head 20b from whipping the gums as the fibers are moved against the teeth of a patient. A cross sectional view of the upper surface of tip 10b, which is in the form of a cup, is featured in FIG. 7B.

Also as depicted in FIG. 7A, the formed tip 10b may be loaded with polishing material 82, such as prophylaxis paste, from a polishing paste reservoir 80. The loaded tip 10b is featured in FIG. 7C. As shown, by protruding outwardly away from their adhesion site on the substrate 22b, the collective fibers 24b form a convenient network of fibers 24b that can at least temporarily maintain prophylaxis material 82 therein.

Figure 7C:
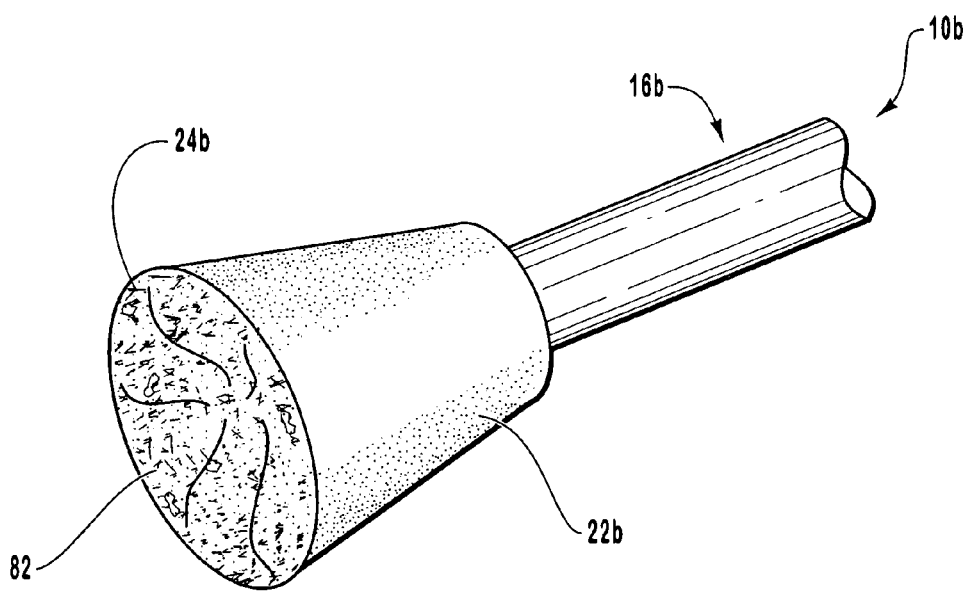
FIG. 7C is a view of the tip of FIG. 7A following the loading of the tip with a paste material 82.

Thus, as shown in the embodiment of FIGS. 7A–C, in one embodiment of the present invention, the flocking fibers 24b located on the polishing head substrate 22b are mounted only on the interior surface 23b thereof, and not on the outer, side portions thereof. This dynamic allows fibers to perform the function of maintaining paste on the polishing head and against the teeth, and allows the fibers to prevent too much friction with the head surface, but minimizes the number of fibers on the outer surface that could contact gums as the head is placed on the teeth adjacent the gums. Thus, no fibers or at least fewer fibers can whip the gums as the fibers on the interior surface contact and polish teeth, such as when the polishing head is placed on the teeth adjacent the gums, or when the outer, non-flocked portion of the polishing head is placed under the gums.

The polishing of a patient's teeth by coupling tip 10b to a dental drive apparatus that moves tip 10b to thereby polish the teeth, such as a handpiece 19 which rotates tip 10b is further depicted in FIG. 8. As shown in FIG. 8, post 16b of tip 10b is coupled (e.g., removably coupled) to handpiece 19.

A variety of different flocking fibers may be employed in the present invention having a variety of different shapes, diameters, and sizes. The flocking fibers employed in the present invention may be coated electrostatic flocking fibers, enhancing the ability of the fibers to receive and respond to an electrical charge (such as AC or DC coated flocking fibers).

Flocking fibers of the present invention may be comprised of a variety of different natural and/or synthetic materials, such as nylon, neoprene, rayon, synthetic polyester, DACRON®, or natural polyester, for example.

In one embodiment, the length of flocking fibers employed in the present invention may be in the range of about 0.005 inch to about 0.3 inch, preferably about 0.01 inch to about 0.1 inch, more preferably about 0.025 inch to about 0.075 inch, for example. However, a variety of different lengths of fibers may be employed and such ranges are provided only by way of example. Thus, one possible length is about 0.03 inch to about 0.04 inch.

Depending upon the desired embodiment, the diameter of flocking fibers employed in the present invention may be in the range of about 0.2 denier to about 100 denier, although a variety of diameters are available depending upon a desired application. For example, fibers having a diameter of about 1.5 denier to about 40 denier may be employed for fine polishing, while fibers having a diameter of about 40 denier to about 100 or about 40 denier to about 80 denier may be employed for a more course polishing, such as a scouring for a yearly cleaning, for example. However, the denier of the fiber is largely dependent upon the type of polishing that may be desired and a variety of different fibers may be employed depending upon the type of polish that is desired. Fibers of the same or different length may vary in diameter to achieve different effects.

According to one technique, the step of forming an adhesive layer comprises depositing a water insoluble adhesive on the surface of the substrate body. As mentioned, however, according to another technique, the adhesive layer is formed by depositing a solvent on at least a portion of the surface of the substrate body, which results in the formation of an adhesive layer that affixes fibers to the substrate body.

A variety of different adhesives may be employed in the present invention depending upon the desired fiber and substrate body to be employed. Examples of useful adhesives include cyanoacrylates, epoxies, urethanes, single and dual part epoxies, single and dual part polyurethanes, ultraviolet curable adhesives and other adhesives used in the art. In one embodiment, a flexible or semi-flexible adhesive is employed for the adhesive layer.

Since the tip of the present invention is designed to be used in the mouth of a patient, the adhesive layer of the present invention is designed to be waterproof upon the hardening thereof to prevent any fluid within the mouth of the patient from damaging the adhesive layer. In one embodiment, the electrostatic flocking is performed at about 25% to about 95% humidity, e.g., at about 65% humidity.

Thus, a method for manufacturing a polishing tip of the present invention comprises: (i) providing a post having a proximal end and a distal end, the proximal end being adapted to be coupled to a dental drive apparatus; (ii) coupling a polishing head substrate to the distal end of the post; and (iii) coupling a plurality of fibers onto the polishing head substrate.

The method of coupling a polishing head substrate to the distal end of the post may be achieved through a variety of different methods, such as by providing a head substrate and attaching a post to the head substrate or by forming the polishing head substrate onto a post (e.g., through a molding process in which the head substrate is molded onto the post). The post may be coupled to the head substrate before or after the coupling of the fibers onto the polishing head substrate.

Other methods may be employed to couple fibers to a polishing head substrate, such as by: welding or fusing the fibers to the substrate, molding the fibers onto the substrate, or forming the substrate with the fibers integrally coupled thereto. However, electrostatic flocking is preferred.

Further information regarding electrostatic flocking, molding processes and additional methods for coupling fibers to a substrate can be obtained from U.S. patent application Ser. No. 09/703,248 entitled Cushioned, Fiber-Covered Dental Delivery Tips, filed on Oct. 30, 2000 and U.S. Pat. No. 6,286,246, entitled Electrostatically Flocked Fishing Lures and Related Systems and Methods, each of which are incorporated herein by reference.

Figure 9A:
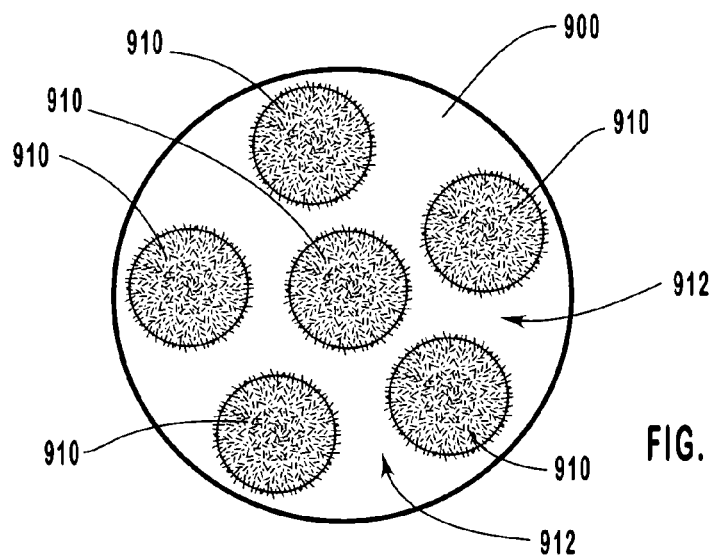
FIGS. 9A, 9B and 9C show various embodiments of flocked fiber bundle configurations on a polishing tip head substrate.
Figure 9B:
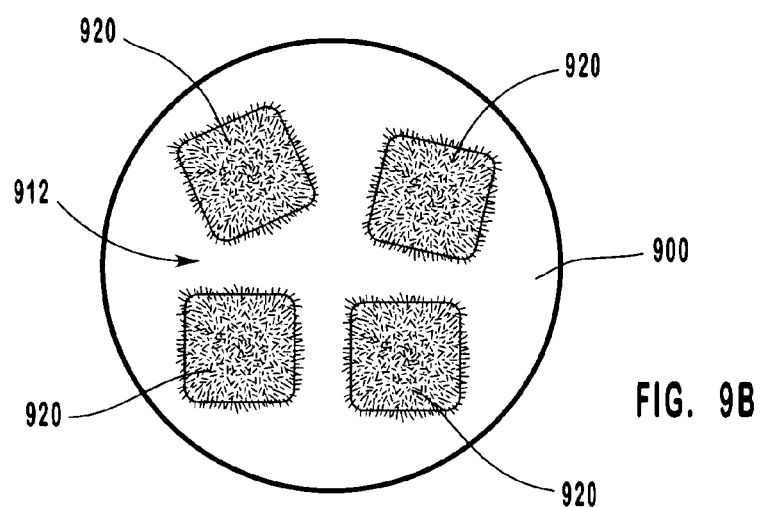
Figure 9C:
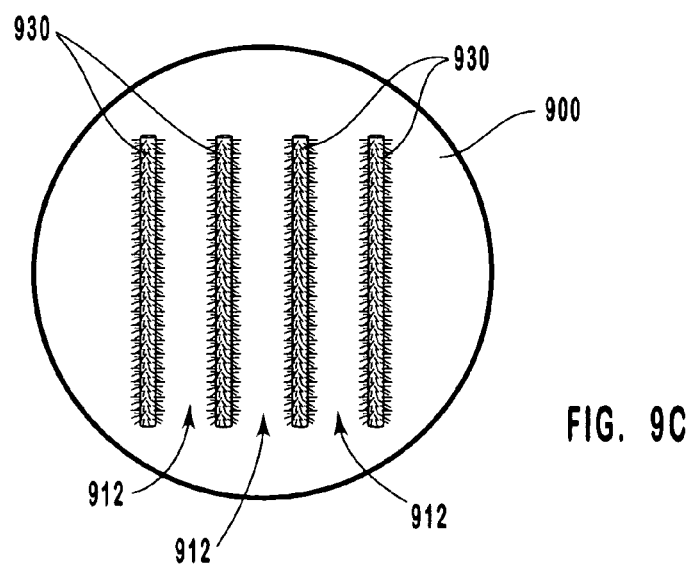

In yet another embodiment of the present invention, shown in FIGS. 9A. 9B and 9C, the fibers may be flocked onto the polishing head substrate in distinct bundles with non-flocked portions 912 of the polishing head substrate 900 separating the bundles of flocked fibers. Such bundles may be in the form of distinct rows 930, circular shaped bundles 910 (e.g., dots), square shaped bundles 920 or bundles having other configurations.

For example, in one embodiment, four rows 930 of flocked fibers on the head substrate are separated by non-flocked portions of head substrate. Optionally, one, two, three, five, six, or any other combination of such rows may be employed.

One advantage to the use of such bundles is that paste material may be temporarily lodged between the bundles (e.g., between rows). In addition, the use of such bundles can conserve the use of adhesive, such that less adhesive (i.e., only the adhesive necessary to form the bundles) may be employed in the manufacturing process.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A polishing tip configured for use during a dental polishing procedure, comprising:
   a post having a proximal end end a distal end, the proximal end comprising means for coupling the post to a rotary dental drive apparatus; and
   a polishing head comprising:
      a polishing head substrate comprised of a flexible material configured to be pressed against a patient's teeth to polish them,
      the polishing head substrate being coupled to the distal end of the post,
      the polishing head substrate further comprising a surface onto which a plurality of individual fibers are coupled to said surface to form flocked surface portions thereon that are disposed at the central inner portion of said surface in order to minimize the number of fibers on the outer edge portion that could contact a patient's gums as the polishing head is place on the teeth adjacent the gums, and
      the flocked surface portions being separated by non-flocked surface portions disposed between the flocked surface portions of the surface.

2. A polishing tip as recited in claim 1, wherein the fibers are flocked onto an adhesive layer provided on the surface of said polishing head substrate so as to be attached to the polishing head substrate by individual attachment sites.

3. A polishing tip as recited in claim 2, wherein the fibers have been electrostatically flocked onto the adhesive layer so as to be substantially parallel to each other.

4. A polishing tip as recited in claim 1, wherein the proximal end is adapted to be coupled to a dental handpiece.

5. A polishing tip as recited in claim 1, wherein the head substrate is in the form of a polishing cup having a cavity configured to receive a paste material therein, the polishing cup further including an interior surface that also includes individual fibers attached thereto by an interior adhesive layer.

6. A polishing tip as recited in claim 1, wherein the post comprises a rigid material.

7. A polishing tip as recited in claim 1, wherein the polishing head substrate comprises an elastomeric material.

8. A method for manufacturing a polishing tip configured for use during a dental polishing procedure, comprising:
   providing a post having a proximal end and a distal end, the proximal end being adapted to be coupled to a dental drive apparatus;
   coupling a polishing head substrate to the distal end of the post, the substrate having a surface and being comprised of a flexible material that is adapted to be pressed against a patient's teeth when polishing them;
   applying an adhesive to interior portions of the surface of the polishing head substrate; and
   electrostatically flocking a plurality of fibers onto interior portions of the surface containing said adhesive to form flocked and non-flocked surface portions on the uolishing bead substrate, the flocked portions being separated by the non-flocked surface portions and disposed at the central inner portion of said surface in order to minimize the number of fibers on the outer edge portion that could contact a patient's gums as the polishing head is placed on teeth adjacent the gums.

\* \* \* \* \*

UNITED STATES PATENT AND TRADEMARK OFFICE
CERTIFICATE OF CORRECTION

PATENT NO. : 6,964,603 B2  Page 1 of 1
APPLICATION NO. : 10/103528
DATED : November 15, 2005
INVENTOR(S) : Fischer et al.

It is certified that error appears in the above-identified patent and that said Letters Patent is hereby corrected as shown below:

Column 2
Line 27, after "aspect of the invention" insert --is--
Line 29, after "of the invention" insert --is--
Line 31, after "aspect of the invention" insert --is--

Column 3
Line 15, insert heading --DETAILED DESCRIPTION OF THE PREFERRED EMBODIMENTS--

Column 4
Line 20, change "deceasing" to --decreasing--

Column 5
Line 47, change "74" to --4--
Line 59, change "20" to --24--

Column 6
Line 3, change "24" to --72--

Column 8
Line 33, after "proximal end" change "end" to --and--

Column 10
Lines 5-6, change "uol-ishing bead" to --pol-ishing head--

Signed and Sealed this

Twenty-eighth Day of August, 2007

JON W. DUDAS
*Director of the United States Patent and Trademark Office*